(12) United States Patent
Bachovchin et al.

(10) Patent No.: US 8,318,668 B2
(45) Date of Patent: *Nov. 27, 2012

(54) STABILIZED GLP-1 ANALOGS

(75) Inventors: William W. Bachovchin, Cambridge, MA (US); David George Sanford, Reading, MA (US)

(73) Assignee: Trustees of Tufts College, Boston, MA (US)

( * ) Notice: Subject to any disclaimer, the term of this patent is extended or adjusted under 35 U.S.C. 154(b) by 584 days.

This patent is subject to a terminal disclaimer.

(21) Appl. No.: 12/066,324

(22) PCT Filed: Sep. 7, 2006

(86) PCT No.: PCT/US2006/034685
§ 371 (c)(1),
(2), (4) Date: Oct. 9, 2008

(87) PCT Pub. No.: WO2007/030519
PCT Pub. Date: Mar. 15, 2007

(65) Prior Publication Data
US 2009/0306338 A1    Dec. 10, 2009

Related U.S. Application Data

(60) Provisional application No. 60/715,322, filed on Sep. 8, 2005.

(51) Int. Cl.
*A61K 38/26* (2006.01)
*A61P 3/10* (2006.01)
(52) U.S. Cl. ............. 514/7.2; 514/6.7; 514/6.8; 514/6.9
(58) Field of Classification Search .................. None
See application file for complete search history.

(56) References Cited

U.S. PATENT DOCUMENTS

2003/0119736 A1* 6/2003 Demuth et al. ............... 514/12
2005/0049177 A1  3/2005 Bachovchin et al.

FOREIGN PATENT DOCUMENTS

| WO | WO 03/011892 | 2/2003 |
| WO | WO 03/020201 | 3/2003 |
| WO | WO 2004/094461 | 11/2004 |
| WO | WO 2004/103390 | 12/2004 |

OTHER PUBLICATIONS

López de Maturana, R. et al., "The Isolated N-terminal Domain of the Glucagon-like Peptide-1 (GLP-1) Receptor Binds Exendin Peptides with Much Higher Affinity than GLP-1," The Journal of Bioglogical Chemistry, 278(12):10195-10200 (2003).
International Search Report for PCT/US2006/34685 dated Sep. 27, 2007.
Supplementary European Search Report for European Patent Application No. 06 81 4219 mailed Sep. 22, 2009.
Doyle, M.E. et al., "The Importance of the Nine-Amino Acid C-terminal Sequence of Exendin-4 for Binding to the GLP-1 Receptor and for Biological Activity," Regulatory Peptides, 114:153-158 (2003).

* cited by examiner

*Primary Examiner* — Gyan Chandra
(74) *Attorney, Agent, or Firm* — Dana M. Gordon; Foley Hoag LLP

(57) ABSTRACT

Polypeptide analogs of the invention that include a) a base amino acid sequence at least 80% identical to one of a GLP-1 fragment; and b) amino acid residues attached to the carboxy terminus of the base amino acid sequence, where the analogs have GLP-1-like activity of longer duration than native GLP-1 and/or the GLP-1 receptor has a greater affinity for the analogs than native GLP-1. Other polypeptide analogs of the invention include a) a base amino acid sequence at least 50% identical to a GLP-1 fragment in which the amino acid residue in the base amino acid sequence corresponding to the $P'_1$ residue of GLP-1 is an amino acid analog having a tetrasubstituted $C_\beta$ carbon; and b) amino acid residues attached to the carboxy terminus of the base amino acid sequence, where the analogs have the properties indicated above. The invention also includes methods of treatment where these analogs are administered.

14 Claims, 7 Drawing Sheets

STABILIZED GLP-1 ANALOGS

RELATED APPLICATIONS

This application claims the benefit of priority to Patent Cooperation Treaty Application number PCT/US2006/034685, filed Sep. 7, 2006; which claims the benefit of priority to U.S. Provisional Patent Application Ser. No. 60/715,322, filed Sep. 8, 2005; the entirety of both of which is incorporated by reference.

BACKGROUND OF THE INVENTION

Polypeptide and peptide therapeutics are widely used in medical practice. Their ease of production, either by recombinant DNA technology or peptide synthesizers, ensures their continued use in a variety of circumstances in the years to come. Accordingly, polypeptide therapeutics, such as hormones, cytokines and growth factors, represent an important class of therapeutic agents. Certain native polypeptides, however, can be inactivated rapidly in vivo via proteolysis or isomerization. Such inactivation can be inconvenient in cases where it is desired to maintain a consistent or sustained blood level of the therapeutic over a period of time, as repeated administrations will then be necessary. In certain instances, one or more of the proteolytic products of the polypeptide can be antagonistic to the activity of the intact polypeptide. In these cases, administration of additional therapeutic alone may be insufficient to overcome the antagonist effect of the proteolytic products.

To further illustrate, one peptide hormone whose prolonged presence in the blood may be beneficial include glucagon-like peptide 1 (GLP-1). GLP-1 is an important polypeptide hormone with regulatory function in glucose metabolism and gastrointestinal secretion and metabolism. Current efforts show that GLP-1 is a growth factor for beta cells in the pancreas and perhaps is involved in cell differentiation in other organs besides pancreas.

GLP-1 is believed to be degraded by members of the post-proline cleaving class of serine proteinase enzymes, such as dipeptidyl peptidase IV (DPP IV). DPP IV is a membrane associated serine peptidase which cleaves N-terminal dipeptides from a peptide chain containing in the penultimate (P1) position, preferably, a proline residue, or an alanine residue if the N-terminal residue (P2) is histidine or a large aromatic such as tyrosine, tryptophan or phenylalanine. The amino terminus sequence of GLP-1 is His-Ala-Glu. Hence, DPP IV has been implicated in the regulation of the activity of GLP-1 in vivo.

DPP IV-mediated removal of Xaa-Ala or Xaa-Pro dipeptides, wherein Xaa is an amino acid residue, from the N-terminus of bioactive peptide hormones such as GLP-1 renders them inactive, or even antagonistic. Accordingly, cleavage and inactivation of peptide hormones by serine proteinases such as DPP IV is one example that illustrates limitations for the use of therapeutic polypeptides; namely, their short duration of action in vivo. For this reason, there is a need in the art for longer-acting peptides with GLP-1-like activity.

SUMMARY OF THE INVENTION

The present invention generally provides GLP-1 analogs that have increased duration of GLP-1-like activity in vivo. The present invention also provides GLP-1 analogs that have increased affinity for the GLP-1 receptor.

In one aspect, the present invention is a polypeptide analog comprising:
  a) a base amino acid sequence at least 80% identical to one of GLP-1-(7-34), GLP-1-(7-35), GLP-1-(7-36) and GLP-1-(7-37) (SEQ ID NOS: 1-4); and
  b) one to fifteen (naturally or non-naturally) occurring amino acid residues attached to the carboxy terminus of the base amino acid sequence,
where the analog has GLP-1-like activity of longer duration in vivo in humans than native GLP-1.

In another aspect, the present invention is a polypeptide analog comprising:
  a) a base amino acid sequence at least 80% identical to one of GLP-1-(7-34), GLP-1-(7-35), GLP-1-(7-36) and GLP-1-(7-37) (SEQ ID NOS: 1-4); and
  b) one to fifteen amino acid residues attached to the carboxy terminus of the base amino acid sequence,
where the GLP-1 receptor has a greater affinity for the analog than native GLP-1. Such analogs also advantageously have GLP-1-like activity of longer duration in vivo in humans than native GLP-1.

In yet another aspect, the present invention is a polypeptide analog comprising:
  a) a base amino acid sequence at least 50% identical to one of GLP-1-(7-34), GLP-1-(7-35), GLP-1-(7-36) and GLP-1-(7-37) (SEQ ID NOS: 1-4) in which the amino acid residue in the base amino acid sequence corresponding to the P'$_1$ residue of GLP-1 is an amino acid analog having a tetrasubstituted C$_\beta$ carbon; and
  b) one to fifteen amino acid residues attached to the carboxy terminus of the base amino acid sequence,
where the analog has GLP-1-like activity of longer duration in vivo in humans than native GLP-1.

In a further aspect, the present invention is a polypeptide analog comprising:
  a) a base amino acid sequence at least 50% identical to one of GLP-1-(7-34), GLP-1-(7-35), GLP-1-(7-36) and GLP-1-(7-37) (SEQ ID NOS: 1-4) in which the amino acid residue in the base amino acid sequence corresponding to the P'$_1$ residue of GLP-1 is an amino acid analog having a tetrasubstituted C$_\beta$ carbon; and
  b) one to fifteen amino acid residues attached to the carboxy terminus of the base amino acid sequence,
where the GLP-1 receptor has a greater affinity for the analog than for native GLP-1. Such analogs also advantageously have GLP-1-like activity of longer duration in vivo in humans than native GLP-1.

The present invention also provides pharmaceutical compositions comprising one or more of the subject analogs. Exemplary pharmaceutical compositions comprise one or more analogs formulated with pharmaceutically acceptable carriers or excipients.

Another aspect of the present invention is a method of treating a disease in a subject comprising administering a therapeutically effective amount of one or more of said analogs. The subject analogs can be administered alone, or can be administered as part of a therapeutic regimen including other therapies appropriate to the specific disease indication. By way of example, administration of an analog for the treatment of diabetes may be used alone, or may be used in combination with modulation of diet and exercise, and/or with administration of insulin. Further exemplary combinatorial methods of treatment comprise administration of an analog and administration of an inhibitor of the particular enzyme or enzymes that cleave the native GLP-1 polypeptide. Such an inhibitor may be specific to the particular enzyme (e.g., a DPP IV specific inhibitor) or may be more generic to the enzyme class (e.g., a serine protease inhibitor).

Another aspect of the present invention is use of the subject analogs for diagnostic purposes.

Another aspect of the present invention is use of the subject analogs for the manufacture of a medicament for treating a disease or condition disclosed herein.

A further aspect of the invention is a method of increasing the in vivo half-life in humans of a peptide at least 80% identical to GLP-1, which includes attaching one to fifteen amino acid residues to the carboxy terminus of the peptide Yet another aspect of the present invention is a method of conducting a business comprising, identifying, manufacturing, marketing, distributing, and/or licensing an analog of the invention, pharmaceutical compositions thereof, and/or kits including the analog.

DETAILED DESCRIPTION OF THE INVENTION

I. Overview

Figure 1:
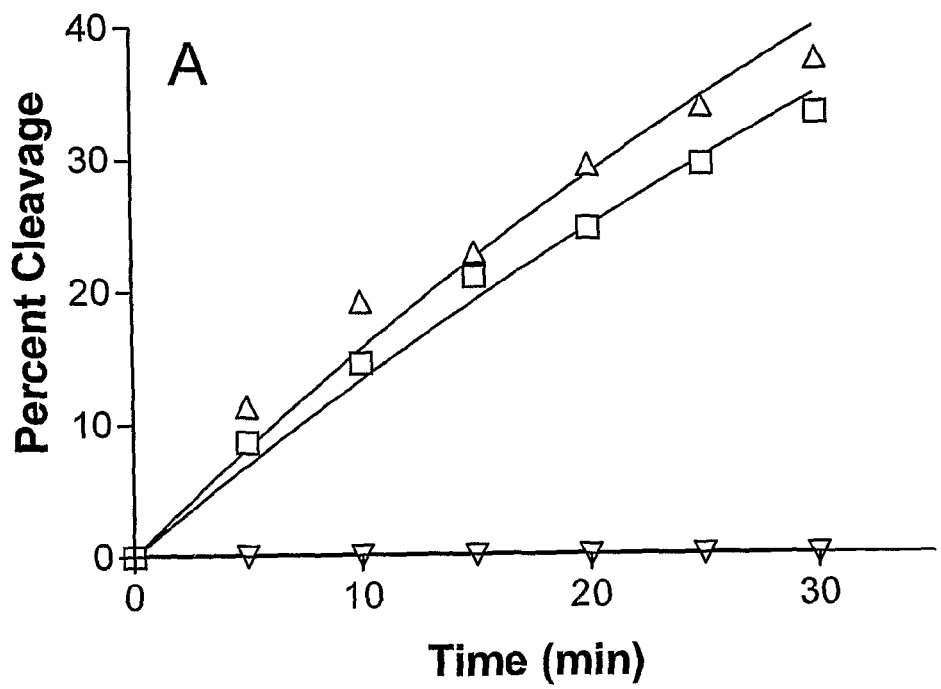
FIG. 1 shows digestion of (A) Ala-Pro-Leu-Ser-Trp-Ser-$NH_2$ (SEQ ID NO: 14) (□), Ala-Pro-Ile-Ser-Trp-Ser-$NH_2$ (SEQ ID NO: 15) (Δ) and Ala-Pro-Tle-Ser-Trp-Ser-$NH_2$ (SEQ ID NO: 16) (∇), incubated with rat DPP IV in 50 mM HEPES, 0.14 M NaCl, pH 8.0 at 37° C.; and (B) GLP-1 (7-36 amide) (■), TPA1B4 (◆), and P1732 (▲) incubated with human DPP IV in 50 mM HEPES, 0.14 M NaCl, pH 8.0 at 30° C. At the indicated times an aliquot was removed, the reaction was stopped by addition of HCl to a pH of 2, and the samples were analyzed by LCMS. Peptide concentrations were 0.1 mM. Percent cleavage was determined by integration of the substrate and product peaks in the MS chromatogram. The data were fit to a single phase exponential equation.
Figure 1:
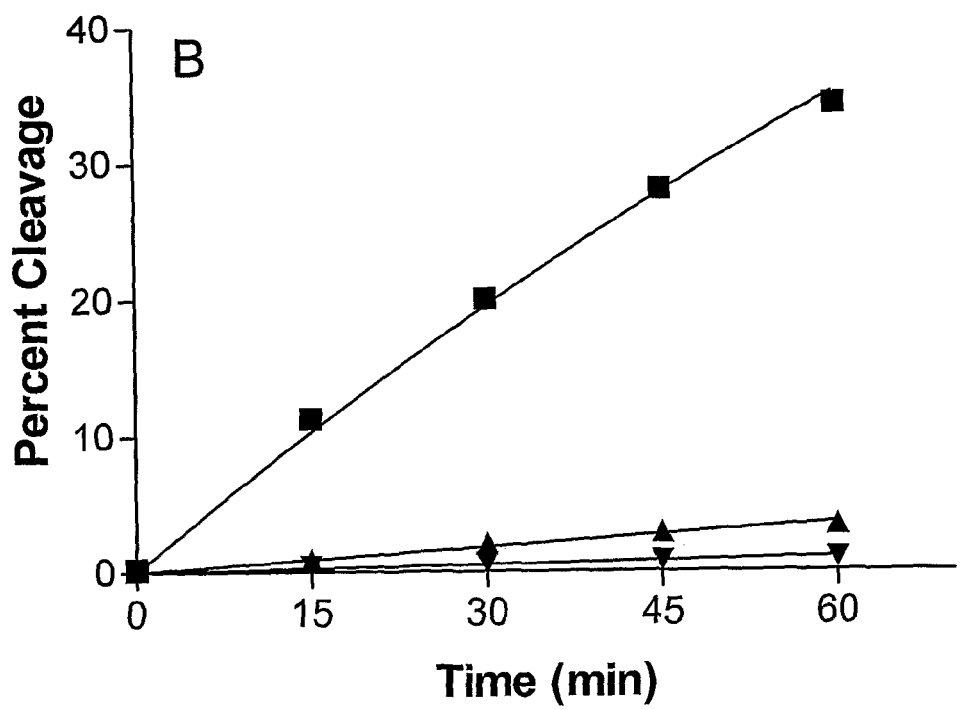

The present invention generally relates to GLP-1 analogs that have increased in vivo half-lives, e.g., resulting from reduced susceptibility to cleavage by proteolytic enzymes and/or increased affinity for the GLP-1 receptor, yet retain the desired activity of GLP-1. In particular, the present invention relates to the discovery that the in vivo half life of a peptide having GLP-L-like activity can be lengthened by attaching one to fifteen (naturally or non-naturally occurring) amino acid residue to the carboxy terminus of the peptide.

GLP-1 analogs of the invention have one to fifteen amino acid residues attached to the carboxy terminal end of the base amino acid sequence. The base amino acid sequence refers to the amino acid sequence prior to modification with the one to fifteen additional amino acid residues. Typically, the base amino acid sequence is at least 50% identical to the sequence of one of GLP-1-(7-34), GLP-1-(7-35), GLP-1-(7-36) and GLP-1-(7-37) (SEQ ID NOS: 1-4), particularly at least 80% identical, at least 90% identical, at least 95% identical or even 100% identical. Typically, sequence identity is measured over the entire length of the relevant sequence. In certain embodiments of the invention, the base amino acid sequence is one of GLP-1-(7-34), GLP-1-(7-35), GLP-1-(7-36) and GLP-1-(7-37) (SEQ ID NOS: 1-4) or differs by only one amino acid residue from one of GLP-1-(7-34), GLP-1-(7-35), GLP-1-(7-36) and GLP-1-(7-37) (SEQ ID NOS: 1-4). The sequences of GLP-1-(7-34), GLP-1-(7-35), GLP-1-(7-36) and GLP-1-(7-37) (SEQ ID NOS: 1-4) are as follows:

```
                                         (SEQ ID NO: 1)
GLP-1-(7-34):   HAEGTFTSDVSSYLEGQAAKEFIAWLVK (SEQ ID NO: 2)
GLP-1-(7-35):   HAEGTFTSDVSSYLEGQAAKEFIAWLVKG (SEQ ID NO: 3)
GLP-1-(7-36):   HAEGTFTSDVSSYLEGQAAKEFIAWLVKGR (SEQ ID NO: 4)
GLP-1-(7-37):   HAEGTFTSDVSSYLEGQAAKEFIAWLVKGRG
```

The added amino acid residues are typically alpha-amino acid residues.

In certain embodiments, one or more (even all) of the added amino acid residues are non-naturally occurring. As used herein, non-naturally occurring amino acids are amino acids other than the 20 amino acids coded for in human DNA. "Non-naturally occurring" is not intended to exclude all amino acids found in organisms (e.g., humans and other mammals) unless specifically indicated.

Exemplary non-naturally occurring amino acids suitable for use in the invention are those having aryl-containing sidechains. In certain embodiments, the aryl-containing sidechain has a bicyclic or polycyclic aryl group. In certain embodiments, the aryl-containing sidechain has two or more aryl groups, such as biphenyl (4-phenyl-phenyl). Exemplary amino acids with non-naturally occurring sidechains include biphenylglycine, biphenylalanine and naphthylglycine, the structures of which are as follows:

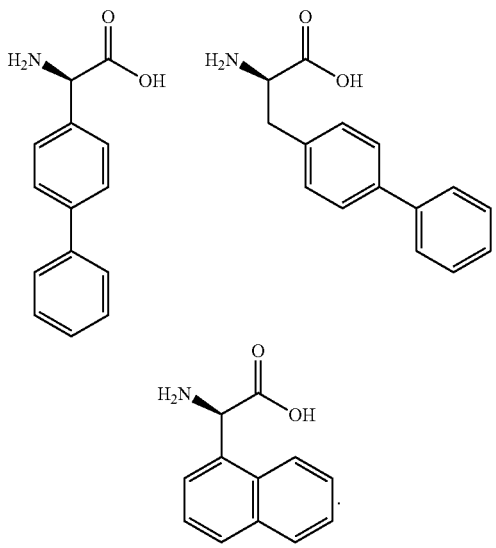

In certain embodiments, the added amino acid residues are all naturally occurring. When all of the added amino acid residues are naturally occurring, the residues are advantageously selected from one or more of those at the carboxy-terminus, residues 31-39, of exendin-4. Exendin-4 is a peptide hormone isolated from the saliva of *Heloderma suspectum* (Gila monster) that has glucose-lowering activity in mammals. Residues 31-39 of exendin-4 are:

```
Pro-Ser-Ser-Gly-Ala-Pro-Pro-Pro-Ser. (SEQ ID NO: 5)
```

Preferably, at least three consecutive residues from residues 31-39, such as Pro-Ser-Ser or the entire nine-residue sequence, are added to the carboxy terminus of a base amino acid sequence. In another preferred embodiment, only Pro is attached to the carboxy terminus.

In certain embodiments of the invention, the base amino acid sequence is modified for post-proline cleaving proteinases at the P'$_1$ position (the residue to the carboxy terminal side of the amide cleavage site). This modification produces GLP-1 analogs with greatly reduced susceptibility to enzyme-mediated cleavage relative to native GLP-1, yet the analogs retain the biological activity of native GLP-1.

Typically, modification of GLP-1 analogs at the P'$_1$ residue (of the cleavage site) involves substitution of an amino acid analog having a tetra-substituted Cβ carbon. Such amino acid analogs can markedly increase the in vivo half-life of the resulting analog, e.g., which may have a longer duration of biological action and/or reduced clearance (e.g., longer serum half-life) relative to the wild-type polypeptide.

While replacing the P'$_1$ residue with another naturally occurring amino acid is contemplated, in preferred embodiments, the P'$_1$ residue is replaced with a non-naturally occurring amino acid analog, and even more preferably, with one which is a structural analog, e.g., retaining similar attributes with respect to steric and/or electronic nature. To illustrate, in certain embodiments the present invention provides a modified polypeptide which is rendered less susceptible to proteolysis by a post-proline cleaving proteinases, such as dipeptidylpeptidase IV (DPP-IV), wherein the polypeptide has been modified at the P'$_1$ position with an amino acid or amino acid analog of Formula I:

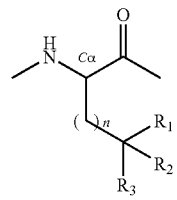

where:

$R_1$ and $R_2$ each independently represent a lower alkyl, heteroalkyl, cycloalkyl, heterocycloalkyl, aryl, alkoxyl, carboxamide, carbonyl, halogen, hydroxyl, amine, or cyano, or $R_1$ and $R_2$ taken together form a ring of 4-7 atoms;

$R_3$ represents a lower alkyl, a heteroalkyl, a cycloalkyl, a heterocycloalkyl, an aryl, amino, alkoxyl, halogen, carboxamide, carbonyl, cyano, thiol, thioalkyl, acylamino, an amido, cyano, nitro, azido, sulfate, sulfonate, sulfonamido, —(CH$_2$)$_m$—R$_4$, —(CH$_2$)$_m$—OH, —(CH$_2$)$_m$—COOH, —(CH$_2$)$_m$—O-lower alkyl, —(CH$_2$)$_m$—O-lower alkenyl, —(CH$_2$)$_n$—O—(CH$_2$)$_m$—R$_4$, —(CH$_2$)$_m$—S-lower alkyl, —(CH$_2$)$_m$—S-lower alkenyl, —(CH$_2$)$_n$—S—(CH$_2$)$_m$—R$_4$, —(CH$_2$)$_m$—N═C(═NH)NH$_2$, —(CH$_2$)$_m$—C(═O—NH)NH$_2$, or —(CH$_2$)$_m$—NH$_2$;

$R_4$ represents, independently for each occurrence, an aryl, aralkyl, cycloalkyl, cycloalkenyl, or a heterocycle;

m=0, 1 or 2; and n=0, 1 or 2.

In certain preferred embodiments, $R_1$ and $R_2$ each independently represents a small hydrophobic group, such as a lower alkyl (preferably methyl, ethyl or propyl, and even more preferably a methyl), a halogen, or a halogenated lower alkyl.

In certain preferred embodiments, $R_3$ represents a lower alkyl, more preferably methyl, ethyl or propyl, and even more preferably a methyl. In other preferred embodiments, $R_3$ represents an aryl, such as phenyl or hydroxyphenyl (preferably para-hydroxy). In yet other preferred embodiments, $R_3$ represents a hydroxyl group. In still other preferred embodiments, $R_3$ represents —(CH$_2$)$_m$—COOH, where m is preferably 0 or 1.

In certain preferred embodiments, n=0.

In certain preferred embodiments of such substrate analogs, the P'$_1$ is an amino acid analog having a tetrasubstituted Cβ carbon, such as represented in Formula II:

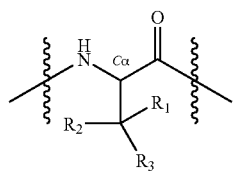

where:

$R_1$ and $R_2$ each independently represent a lower alkyl, heteroalkyl, cycloalkyl, heterocycloalkyl, aryl, alkoxyl, carbonyl, carboxamide, halogen, hydroxyl, amine, or cyano, or $R_1$ and $R_2$ taken together form a ring of 4-7 atoms;

$R_3$ represents a lower alkyl, a heteroalkyl, amino, alkoxyl, halogen, carboxamide, carbonyl, cyano, thiol, thioalkyl, acylamino, nitro, azido, sulfate, sulfonate, sulfonamido, —$(CH_2)_m$—$R_4$, —$(CH_2)_m$—OH, —$(CH_2)_m$—COOH, —$(CH_2)_m$—O-lower alkyl, —$(CH_2)_m$—O-lower alkenyl, —$(CH_2)_n$—O—$(CH_2)_m$—$R_4$, —$(CH_2)_m$—S-lower alkyl, —$(CH_2)_m$—S-lower alkenyl, —$(CH_2)_n$—S—$(CH_2)_m$—$R_4$, —$(CH_2)_m$—N—C(=NH)NH$_2$, —$(CH_2)_m$—C(=O)NH$_2$, or —$(CH_2)_m$—NH$_2$;

$R_4$ represents, independently for each occurrence, an aryl, aralkyl, cycloalkyl, cycloalkenyl, or non-aromatic heterocyclyl; and m=0, 1 or 2.

In certain embodiments, $R_1$ and $R_2$ are each independently represent a lower alkyl or a halogen; $R_3$ represents a lower alkyl, an aryl, a hydroxyl group, —$(CH_2)_m$COOH, —$(CH_2)_m$—NH$_2$, —$(CH_2)_m$—N—C(=NH)NH$_2$, $(CH_2)_m$—C(=O)NH$_2$, —SH, or —$(CH_2)_m$—S—CH$_3$; and m=0, 1 or 2.

In certain preferred embodiments, $R_1$ and $R_2$ each independently represent a methyl, ethyl or propyl, and even more preferably a methyl.

In certain preferred embodiments, $R_3$ represents a lower alkyl, more preferably methyl, ethyl or propyl, and even more preferably a methyl. In other preferred embodiments, $R_3$ represents an aryl, such as a phenyl, hydroxyphenyl (preferably para-hydroxy), indole or imidazole. In yet other preferred embodiments, $R_3$ represents a hydroxyl group. In certain preferred embodiments, $R_3$ represents —COOH or —CH$_2$—COOH. In still other preferred embodiments, $R_3$ represents —CH$_2$—CH$_2$—N—C(=NH)NH$_2$, —CH$_2$—C(=O)NH$_2$, —CH$_2$—CH$_2$—C(=O)NH$_2$, —SH, or —CH$_2$—S—CH$_3$.

Exemplary base amino acid sequences having a modified $P'_1$ residue are shown in Table 1, where X indicates the position of the modified $P'_1$ residue:

TABLE 1

|  | Native sequence | Exemplary Analog |
|---|---|---|
| Human glucagon-like peptide GLP-1(7-37) | HAE*GTFTSDVSSYLEGQAAKEF IAWLVKGRG (SEQ ID NO: 4) | HAXGTFTSDVSSYLEGQAAKEFIA WLVKGRG (SEQ ID NO: 6) |
| Human glucagon-like peptide 1: GLP-1 (7-36)NH$_2$ | HAE*GTFTSDVSSYLEGQAAKEF IAWLVKGR-NH$_2$ (SEQ ID NO: 3) | HAXGTFTSDVSSYLEGQAAKEFIA WLVKGR-NH$_2$ (SEQ ID NO: 7) |
| Exendin-4 (GLP-1 analog) | HGE*GTFTSDLSKQMEEEAVRLF IEWLKNGGPSSGAPPPS-NH$_2$ (SEQ ID NO: 8) | HGXGTFTSDLSKQMEEEAVRLFIE WLKNGGPSSGAPPPS-NH$_2$ (SEQ ID NO: 9) |

More generally, the present invention specifically contemplates the generation of analogs for GLP-1 that have an amino acid sequence:

Xaa-Ala-Yaa-R or

Xaa-Pro-Yaa-R' where Xaa and Yaa represent amino acid residues, and R and R', independently for each occurrence, represent polypeptide chains having GLP-1-like activity and comprising 1 to about 100 amino acid residues, where the analog sequence Yaa is replaced by an amino acid residue represented by Formula I or Formula II. The invention contemplates the modification of variant polypeptides that differ in sequence from GLP-1 in order to produce variant $P'_1$ analogs. Such variants are at least 80%, 85%, 90%, 95%, 97%, 99%, or greater than 99% identical to GLP-1-(7-36).

In certain embodiments, R is a polypeptide having an amino acid sequence selected from:

GTFTSDVSSYLEGQAAKEFIAWLVKGRG, (SEQ ID NO: 10)
and

GTFTSDVSSYLEGQAAKEFIAWLVKGR-NH$_2$, (SEQ ID NO: 11)

or a sequence that differs by 5 or fewer amino acid residues thereto, even more preferably differs by no more than 4, 3, or even 2 amino acid residues.

A preferred base amino acid sequence is:

(SEQ ID NO: 12)
His-Ala-Xaa-Gly-Thr-Phe-Thr-Ser-Asp-Val-Ser-Ser-
Tyr-Leu-Glu-Gly-Gln-Ala-Ala-Lys-Glu-Phe-Ile-Ala-
Trp-Leu-Val-Lys-Gly-Arg, where Xaa is beta-dimethylaspartate or tert-leucine, particularly beta-dimethylaspartate. Amino acids advantageously attached to this base amino acid sequence include biphenylglycine, Pro-Ser-Ser and Pro-Ser-Ser-Gly-Ala-Pro-Pro-Pro-Ser (SEQ ID NO: 5).

II. Definitions

The binding site for a peptide substrate consists of a series of "specificity subsites" across the surface of the enzyme. The term "specificity subsite" refers to a pocket or other site on the enzyme capable of interacting with a portion of a substrate for the enzyme.

In discussing the interactions of peptides and protein substrates with proteinases, e.g., serine and cysteine proteinases and the like, the present application utilizes the nomenclature of Schechter and Berger [(1967) *Biochem. Biophys. Res. Commun.* 27:157-162)]. The individual amino acid residues of a substrate or inhibitor are, from amino terminus to carboxy terminus, designated —$P_2$—$P_1$—$P'_1$—$P'_2$—, etc. and the corresponding subsites of the enzyme are designated $S_2$, $S_1$, $S'_1$, $S'_2$, etc. The scissile bond of the substrate is the amide bond linking the $P_1$ and $P'_1$ residues.

A "$P'_1$ residue" refers to the amino acid residue of a substrate polypeptide that becomes the new amino terminus of product polypeptide resulting from proteinase-mediated cleavage of the amide backbone of the substrate polypeptide. To further illustrate, a substrate polypeptide includes an amide backbone bond that is subject to a proteolytic reaction represented by the general scheme:

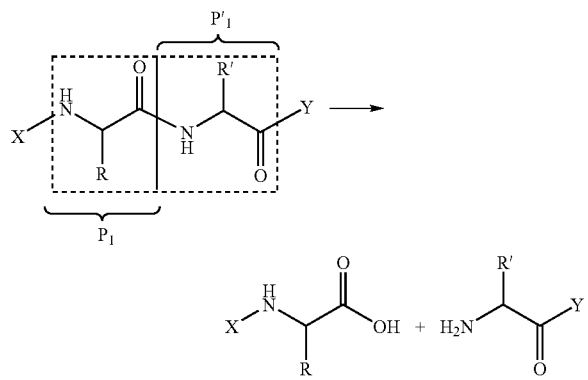

By the term "amino acid residue" is meant an amino acid, typically an alpha-amino acid. In general the abbreviations used herein for designating the naturally occurring amino acids are based on recommendations of the IUPAC-IUB Commission on Biochemical Nomenclature (see Biochemistry (1972) 11:1726-1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group.

The term "amino acid side chain" is that part of an amino acid residue exclusive of the backbone, as defined by K. D. Kopple, "Peptides and Amino Acids", W. A. Benjamin Inc., New York and Amsterdam, 1966, pages 2 and 33; examples of such side chains of the common amino acids are —CH$_2$CH$_2$SCH$_3$ (the side chain of methionine), —CH$_2$(CH$_3$)—CH$_2$CH$_3$ (the side chain of isoleucine), —CH$_2$CH(CH$_3$)$_2$ (the side chain of leucine) or —H (the side chain of glycine). These sidechains are pendant from the backbone Cα carbon.

The term "tetrasubstituted Cβ carbon" refers to a carbon atom which is (i) directly pendant from the Cα carbon of the amino acid backbone, and (ii) bears four substituents (including the Cα carbon), none of which is hydrogen.

As used herein, "protein" is a polymer consisting essentially of a combination of any of the 20 amino acids. Although "polypeptide" is often used in reference to relatively large proteins, and "peptide" is often used in reference to small protein, usage of these terms in the art overlaps and is varied. Unless evident from the context, the terms "peptide(s)", "protein(s)" and "polypeptide(s)" are used interchangeably herein.

The International Union of Biochemistry and Molecular Biology (1984) has recommended using the term "peptidase" for the subset of peptide bond hydrolases (Subclass E.C 3.4.). The widely used term "protease" is synonymous with "peptidase", and they are used interchangeably herein. Peptidases comprise two groups of enzymes: the endopeptidases and the exopeptidases. Endopeptidases cleave peptide bonds at points within a protein, and exopeptidases remove amino acids sequentially from either the amino or carboxy terminus.

The term "proteinase" is also used as a synonym for endopeptidase. Proteinases are classified according to their catalytic mechanisms. Four mechanistic classes have been recognized by the International Union of Biochemistry and Molecular Biology: serine proteinases, cysteine proteinases, aspartic proteinases, and metalloproteinases.

The term "agonist", as used herein, is meant to refer to an analog that retains the bioactivity of the native substrate of interest (e.g., GLP-1) so as to produce a similar biological effect when administered to an animal.

The term "antagonist" refers to an analog that does not retain the bioactivity of the native substrate of interest (e.g., GLP-1), or at least at a reduced level of activity relative to the native substrate, and inhibits the biological action of the native substrate.

The term "analog" refers to a molecule substantially similar in function to a native peptide or protein or a fragment thereof.

"Instruction(s)" as used herein means a product label and/or documents describing relevant materials or methodologies pertaining to use of a kit or packaged pharmaceutical. These materials may include any combination of the following: background information, list of components, proposed dosages, warnings regarding possible side effects, instructions for administering the drug, technical support, and any other related documents.

An "effective amount" of a compound, e.g., such as an analog of the present invention, with respect to use in treatment, refers to an amount of the analog in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "alkyl" refers to a fully saturated branched or unbranched carbon chain radical having the number of carbon atoms specified, or up to 30 carbon atoms if no specification is made. For example, a "lower alkyl" refers to an alkyl having from 1 to 10 carbon atoms, such as methyl, ethyl, propyl, butyl, pentyl, hexyl, heptyl, and octyl, and those which are positional isomers of these alkyls. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both unsubstituted and substituted alkyl chains, the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, a cyano, a nitro, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxyls, alkylthios, aminoalkyls, carbonyl-substituted alkyls, —$CF_3$, —CN, and the like.

Unless the number of carbons is otherwise specified, "lower alkyl", as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

A "heteroalkyl group" is an alkyl group where one or more of the internal (i.e., not terminal) carbon atoms is replaced by a heteroatom, such as nitrogen, oxygen, sulfur, phosphorus, selenium or silicon. Typically, the heteroatom is nitrogen, oxygen or sulfur. A "heterocycloalkyl group" is the analogous cyclic alkyl group where a carbon atom is replaced by a heteroatom.

The term "carbocycle", as used herein, refers to an aromatic or non-aromatic ring in which each atom of the ring is carbon.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

"Alkenyl" refers to any branched or unbranched unsaturated carbon chain radical having the number of carbon atoms specified, or up to 26 carbon atoms if no limitation on the number of carbon atoms is specified; and having 1 or more double bonds in the radical. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl and tetracosenyl, in their various isomeric forms, where the unsaturated bond(s) can be located anywhere in the radical and can have either the (Z) or the (E) configuration about the double bond(s).

The term "alkynyl" refers to hydrocarbyl radicals of the scope of alkenyl, but having 1 or more triple bonds in the radical.

The terms "alkoxyl" or "alkoxy" as used herein refers to an alkyl group, as defined below, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_1$, where m and $R_1$ are described below.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, or the like.

The term "alkylthio" refers to an alkyl group, as defined above, having a sulfur radical attached thereto. In preferred embodiments, the "alkylthio" moiety is represented by one of —(S)-alkyl, —(S)-alkenyl, —(S)-alkynyl, and —(S)—$(CH_2)_m$—$R_1$, wherein m and $R_1$ are defined below. Representative alkylthio groups include methylthio, ethylthio, and the like.

As used herein, the term "nitro" means —$NO_2$; the term "halogen" designates —F, —Cl, —Br or —I; the term "sulfhydryl" or "thiol" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formulae:

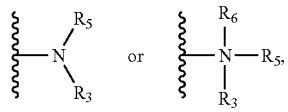

wherein $R_3$, $R_5$ and $R_6$ each independently represent a hydrogen, an alkyl, an alkenyl, —$(CH_2)_m$—$R_1$, or $R_3$ and $R_5$ taken together with the N atom to which they are attached complete a heterocycle having from 4 to 8 atoms in the ring structure; $R_1$ represents an alkenyl, aryl, cycloalkyl, a cycloalkenyl, a heterocyclyl or a polycyclyl; and m is zero or an integer in the range of 1 to 8. In preferred embodiments, only one of $R_3$ or $R_5$ can be a carbonyl, e.g., $R_3$, $R_5$ and the nitrogen together do not form an imide. In even more preferred embodiments, $R_3$ and $R_5$ (and optionally $R_6$) each independently represent a hydrogen, an alkyl, an alkenyl, or —$(CH_2)_m$—$R_1$. Thus, the term "alkylamine" as used herein means an amine group, as defined above, having a substituted or unsubstituted alkyl attached thereto, i.e., at least one of $R_3$ and $R_5$ is an alkyl group. In certain embodiments, an amino group or an alkylamine is basic, meaning it has a pK$_a$≧7.00. The protonated forms of these functional groups have pK$_a$s relative to water above 7.00.

The term "carbonyl" is art-recognized and includes such moieties as can be represented by the general formula:

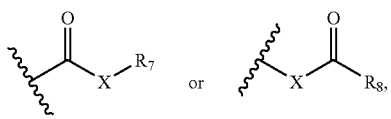

wherein X is a bond or represents an oxygen or a sulfur, and R$_7$ represents a hydrogen, an alkyl, an alkenyl, —(CH$_2$)$_m$—R$_1$, or a pharmaceutically acceptable salt, R$_8$ represents a hydrogen, an alkyl, an alkenyl or —(CH$_2$)$_m$—R$_1$, where m and R$_1$ are as defined above. Where X is an oxygen and R$_7$ or R$_8$ is not hydrogen, the formula represents an "ester". Where X is an oxygen, and R$_7$ is as defined above, the moiety is referred to herein as a carboxyl group, and particularly when R$_7$ is a hydrogen, the formula represents a "carboxylic acid". Where X is an oxygen, and R$_8$ is hydrogen, the formula represents a "formate". In general, where the oxygen atom of the above formula is replaced by sulfur, the formula represents a "thiocarbonyl" group. Where X is a sulfur and R$_7$ or R$_8$ is not hydrogen, the formula represents a "thioester" group. Where X is a sulfur and R$_7$ is hydrogen, the formula represents a "thiocarboxylic acid" group. Where X is a sulfur and R$_8$ is hydrogen, the formula represents a "thioformate" group. On the other hand, where X is a bond, and R$_7$ is not hydrogen, the above formula represents an "acyl" group. Where X is a bond, and R$_7$ is hydrogen, the above formula represents an "aldehyde" group.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

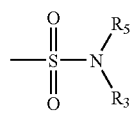

in which R$_3$ and R$_5$ are as defined above.

The term "sulfate" is art recognized and includes a moiety that can be represented by the general formula:

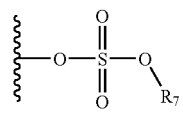

in which R$_7$ is as defined above.

The term "sulfonamido" is art recognized and includes a moiety that can be represented by the general formula:

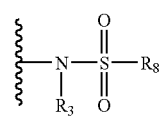

in which R$_2$ and R$_4$ are as defined above.

The term "sulfonate" is art-recognized and includes a moiety that can be represented by the general formula:

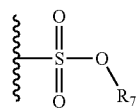

in which R$_7$ is an electron pair, hydrogen, alkyl, cycloalkyl, or aryl.

The terms "sulfoxido" or "sulfinyl", as used herein, refers to a moiety that can be represented by the general formula:

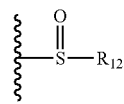

in which R$_{12}$ is selected from hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

III. Exemplary Embodiments

(a) Characteristics of Analogs

In many embodiments, the analog will be selected to retain one or more of the in vitro or in vivo activity of the native substrate. The in vitro and in vivo activities may be measured using any protocol available to one of ordinary skill that is appropriate for the particular analog. Exemplary functional activities that can be measured to ascertain whether an analog maintains the same or similar functional activity include ability of the analog to bind its receptor(s) in a cell based or cell free assay, ability of the analog to induce a change (e.g., proliferation, differentiation, survival, growth, migration, etc) in a cell responsive to GLP-1, ability of the analog to modulate the expression of one or more other genes or proteins in a cell responsive to GLP-1.

In certain embodiments, the analog has substantially similar activity as native GLP-1 or a fragment thereof (e.g., about 80%, 90%, 100%, 110%, or 120% as active as the native GLP-1). In some embodiment, the analog is less active than native GLP-1 (e.g., about 50%, 60%, 70%, or 75% as active as the native polypeptide). We note that an analog that is somewhat less active may be useful, such as in vivo or in cell culture, if the decrease in activity still provides the ability to provide a sufficient local concentration of analog for a sufficient period of time. Thus, an increase in half-life obtained, for example, by proteinase resistance could off-set the decrease in activity caused by the construction of the analog. In still other embodiment, the analog is more active that native GLP-1 (e.g., about 130%, 150%, 175%, 200%, 300%, 500%, 800%, or even 1000% as active as native GLP-1). In any of the foregoing, by "activity" is meant one or more functions of native GLP-1. For example, an activity (e.g., a biological function) of an analog may be receptor binding, ability to act as a transcriptional activator or repressor, the ability to participate in a particular signal transduction pathway, or the ability to influence cell behavior (e.g., proliferation, differentiation, survival, or migration).

Such activities may be expressed, for example, as relative binding constants (such as for receptor binding), effective concentrations ($EC_{50}$) and/or effective doses ($ED_{50}$).

Exemplary analogs have an increased half life (or duration of action) in comparison to native GLP-1 (in vitro and/or in vivo). However, it will be generally appreciated that various analogs will have different half-lives (as well as a different change in half-life in comparison to native GLP-1). The in vitro and/or in vivo half-life (or duration of action) can be readily measured by one of skill in the art using standard methods, for example, the time course of glucose lowering effects. In certain embodiments, the analog has an in vitro or in vivo half life (duration of action) that is about a factor of 0.1, 0.2, 0.3, 0.4, 0.5, 0.6, 0.7, 0.8, 0.9, 1.0, 1.3, 1.5, 2, 3, 5, 10, 25, 30, 50, 75, 100, or even greater than 100 times the in vitro and/or in vivo half-life of the native polypeptide under similar half-life measurement assay conditions.

(b) Synthesis of Peptide Hormone Analogs

The analogs of the invention can be prepared by standard solid phase synthesis; see, e.g., Stewart, J. M., et al., Solid Phase Synthesis (Pierce Chemical Co., 2d ed. 1984). As is generally known, peptides of the requisite length can be prepared using commercially available equipment and reagents following the manufacturers' instructions for blocking interfering groups, protecting the amino acid to be reacted, coupling, deprotection, and capping of unreacted residues. Suitable equipment can be obtained, for example, from Applied BioSystems in Foster City, Calif., or Biosearch Corporation in San Raphael, Calif.

In a preferred method, the analogs are synthesized using standard automated solid-phase synthesis protocols employing t-butoxycarbonyl-alpha-amino acids with appropriate side-chain protection. Completed analog is removed from the solid phase support with simultaneous side-chain deprotection using the standard hydrogen fluoride method. Crude analogs are further purified by semi-preparative reverse phase-HPLC (Vydac $C_{18}$) using acetonitrile gradients in 0.1% trifluoroacetic acid (TFA). The analogs are vacuum dried to remove acetonitrile and lyophilized from a solution of 0.1% TFA in water. Purity is verified by analytical RP-HPLC. The peptides can be lyophilized and then solubilized in either water or 0.01M acetic acid at concentrations of 1-2 mg/mL by weight.

The use of the aforementioned synthetic methods is needed if nonencoded amino acids or the D forms of amino acids occur in the analogs. However, for analogs which can be gene-encoded, recourse can also be had to recombinant techniques using readily synthesized DNA sequences in commercially available expression systems.

(c) Functional Assays

A variety of methods for assessing whether a candidate analog is resistant to proteolysis are available in the art. For example, the ability of a particular proteinase to cleave an analog can be measured in a cell free system in vitro. In one such embodiment of a cell free assay system, candidate substrate (e.g., an analog and/or a native polypeptide) is end labeled with a detectable label such as radioactivity. Labeled substrate is incubated in the presence of proteinase. Over time, samples of the reaction mixture can be stopped and run on a gel. A shift in the size of the radioactive band indicates that the polypeptide is cleaved by the proteinase, and the rate at which this shift occurs indicates the rate at which the polypeptide is cleaved by the proteinase. This rate can be compared to that observed with the native polypeptide.

To further illustrate, an exemplary experiment to test a particular analog involves the following. The native polypeptide (GLP-1) and the putative analog are each radioactively labelled (note: for the purposes of labeling, all that is necessary is that cleavage of the polypeptide produces a radioactive fragment which differs in size from the full length labeled polypeptide). The labeled native polypeptide and analog are incubated with the particular proteinase. Following incubation, both native polypeptide and analog are separated by gel electrophoresis, and the migration of the labeled species is examined. Since the particular proteinase is known to cleave the native polypeptide, one would expect to see a shift in the size of the labeled fragment of the native polypeptide (before and after incubation with enzyme) with the smaller fragment corresponding to a cleavage product. However, if the analog is resistant to proteolysis, this shift in mobility following incubation with proteinase will either not occur, or will occur much more slowly than occurs for the proteolysis of the native protein.

The relative ability of a proteinase to cleave an analog in comparison to a native polypeptide can also be assessed in a cell based in vitro system. In one such cell based assay, a cell which expresses a given proteinase is contacted with a native polypeptide or an analog such that the native polypeptide or analog is present in the cell. Much like in the cell free assay described above, the native polypeptide and analog are detectably labelled. Cleavage of the native polypeptide and the analog can be measured and compared by extracting protein from the cells and measuring the migration of labeled protein.

In a further example of a cell-based assay, a cell which does not express a given proteinase is contacted with a detectably labeled native polypeptide or analog such that the native polypeptide or analog is expressed in the cell. The cell is further contacted with the particular proteinase such that the proteinase is expressed in the cell. Cleavage of the native polypeptide and the analog can be measured and compared by extracting protein from the cells and measuring the migration of labeled protein.

In any of the aforementioned cell based assays, the invention contemplates the use of any of a number of primary cells or cell lines. In some instances, it may be advantageous to select a particular cell or cell line in which to conduct in vitro analysis. For example, it may be advantageous in some instances to select a cell line that is more closely related to the cell type in which one eventually wishes to use the analog. However, in other instances, it may be most useful to perform initial screening and testing of candidate analogs in a possibly unrelated cell type or cell line selected primarily based on convenience, and perform later safety and efficacy testing in more specific cell lines or in animal models as needed.

In addition to cell-free and cell-based assays, the proteinase resistance of a particular analog can be measured in vivo using any of a number of animal models. Initial testing of the proteolysis of a given analog can be assessed in wildtype animals. During such initial testing, the potential positive or negative effects of the analog are not the question, but rather the question is whether a particular analog is resistant to proteolysis. Once a particular analog is shown to be resistant to proteolysis using any of the cell free, cell based, or in vivo assays described above, further in vitro and in vivo testing of the analog can be conducted to ascertain the therapeutic effectiveness of the analog.

Additional assays can be used to evaluate the specific functional activity of an analog. Such assays can be selected based on the particular analog. For the present GLP-1 analogs, the functional activity of the analog can be assessed by measuring the ability of the analog to bind its receptor in a cell-free or cell-based assay, and comparing this to the ability of the native peptide hormone. In any of these examples, functional activity can also be measured in animal models, such as those assaying blood glucose or insulin levels.

The following illustrative example provides potential methods of assessing a functional activity of analogs.

1. Assays of Insulinotropic Activity

Active GLP-1 peptides, 7-34, 7-35, 7-36, and 7-37, have insulinotorpic activity, and the invention provides methods for making peptide analogs of these active GLP-1 peptides. The resistance of GLP-1 peptide analogs to proteolysis can be readily measured. Additionally, the functional activity of the GLP-1 peptide analogs can be demonstrated by examining the insulinotropic properties of the peptide hormone analogs. Insulinotrophic activity can be determined, for example, by providing a given peptide analog to animal cells, or injecting that analog into animals and monitoring the release of immunoreactive insulin (IRI) into the media or circulatory system of the animal, respectively. The presence of IRI can be detected through the use of a radioimmunoassay which can specifically detect insulin.

The db/db mouse is a genetically obese and diabetic strain of mouse. The db/db mouse develops hyperglycemia and hyperinsulinemia concomitant with its development of obesity and thus serves as a model of obese type 2 diabetes (NIDDM). The db/db mice can be purchased from, for example, The Jackson Laboratories (Bar Harbor, Me.). In an exemplary embodiment, for treatment of the mice with a regimen including a peptide hormone analog or control, sub-orbital sinus blood samples are taken before and at some time (e.g., 60 minutes) after dosing of each animal. Blood glucose measurements can be made by any of several conventional techniques, such as using a glucose meter. The blood glucose levels of the control and peptide hormone analog dosed animals are compared The metabolic fate of exogenous GLP-1 analog can also be followed in either nondiabetic or type II diabetic subjects, and the effect of a candidate analog determined. For instance, a combination of high-pressure liquid chromatography (HPLC), specific radioimmunoassays (RIAs), and an enzyme-linked immunosorbent assay (ELISA), can be used, whereby intact biologically active GLP-1 and its metabolites can be detected. See, for example, Deacon et al. (1995) *Diabetes* 44:1126-1131. To illustrate, after GLP-1 analog administration, the intact peptide can be measured using an $NH_2$-terminally directed RIA or ELISA, while the difference in concentration between these assays and a COOH-terminal-specific RIA allowed determination of $NH_2$-terminally truncated metabolites. Without the analog, subcutaneous GLP-1 is rapidly degraded in a time-dependent manner, forming a metabolite which co-elutes on HPLC with GLP-1-(9-36) amide and has the same immunoreactive profile. For instance, thirty minutes after subcutaneous GLP-1 administration to diabetic patients (n=8), the metabolite accounted for 88.5+ 1.9% of the increase in plasma immunoreactivity determined by the COOH-terminal RIA, which was higher than the levels measured in healthy subjects (78.4+3.2%; n=8; P<0.05). See Deacon et al., supra. Intravenously infused GLP-I was also extensively degraded.

Other methods of measuring insulinotropic activities of GLP-1 analogs are disclosed in U.S. Pat. No. 5,545,618.

(d) Pharmaceutical Preparations

For therapeutic use, the chosen analog is formulated with a carrier that is pharmaceutically acceptable and is appropriate for administering a therapeutically effective amount of the analog to a subject using a dosage adapted for a chosen route of administration, i.e., oral, intravenous, or parenteral, so as to deliver the peptide to the desired tissue. In certain embodiments, the analogs are non-pyrogenic, i.e., do not trigger elevation of a patient's body temperature by more than a clinically acceptable amount. Suitable pharmaceutically acceptable carriers are those used conventionally with peptide-based drugs, such as diluents, excipients and the like. Reference may be made to "Remington's Pharmaceutical Sciences", 17th Ed., Mack Publishing Company, Easton, Pa., 1985, for guidance on drug formulations generally. In one embodiment of the invention, the compounds are formulated for administration by infusion, e.g., when used as liquid nutritional supplements for patients on total parenteral nutrition therapy, or by injection, e.g., sub-cutaneously, intramuscularly or intravenously, and are accordingly utilized as aqueous solutions in sterile and pyrogen-free form and optionally buffered to physiologically tolerable pH, e.g., a slightly acidic or physiological pH. Thus, the compounds may be administered in a vehicle such as distilled water or, more desirably, in saline, phosphate buffered saline or 5% dextrose solution. Water solubility of an analog can be enhanced, if desired, by incorporating a solubility enhancer, such as acetic acid or sodium hydroxide.

The analogs of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, or toluenesulfonic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids).

A therapeutically effective amount of an analog of this invention and a pharmaceutically acceptable carrier substance (e.g., magnesium carbonate, lactose, or a phospholipid with which the therapeutic analog can form a micelle) together form a therapeutic composition (e.g., a pill, tablet, capsule, or liquid) for administration (e.g., orally, intravenously, transdermally, pulmonarily, vaginally, subcutaneously, nasally, iontophoretically, intratracheally, intracranially, intramyocardially, intraperidardially, intramuscularly) to a subject. A pill, tablet, or capsule that is to be administered orally can be coated with a substance for protecting the active composition from the gastric acid or intestinal enzymes in the stomach for a period of time sufficient to allow it to pass undigested into the small intestine. The therapeutic composition can also be in the form of a biodegradable or nonbiodegradable sustained release formulation for subcutaneous or intramuscular administration. See, e.g., U.S. Pat. Nos. 3,773, 919 and 4,767,628 and PCT Publication No. WO 94/15587. Continuous administration can also be achieved using an implantable or external pump (e.g., INFUSAID™ pump). The administration can also be conducted intermittently, e.g., single daily injection, or continuously at a low dose, e.g., sustained release formulation.

Therapeutic or diagnostic compositions of the invention are administered to an individual in amounts sufficient to treat or diagnose disorders. The effective dose of a peptide of the present invention for treating the above-mentioned diseases or disorders varies depending upon the manner of administration, the age and the body weight of the subject, and the condition of the subject to be treated, and ultimately will be decided by the attending physician or veterinarian.

Also contemplated within the scope of this invention is a peptide covered by the above generic formula for use in treating diseases or disorders associated with aberrant glucose metabolism, lipid metabolism or eating disorder.

Other features and advantages of the present invention will be apparent from the detailed description and from the claims.

(e) Methods of Use

1. Diagnostic Uses

The analogs of the invention may be used in radiolabeled or unlabeled form to diagnose or treat a variety of disease states including but not limited to those associated with glucose metabolism, lipid metabolism and food intake.

Preferably, radiolabeled complexes of the compounds of the invention are used for such diagnoses and treatments. Radiolabeled embodiments, of the compounds of the invention may be used in radioisotope guided surgery, as described in WO 93/18797 and in Woltering, et al. (1994) Surgery 116, 1139-1147. In a preferred embodiment, a complex of a gamma-emitting radionuclide such as $^{99}$Tc and a compound of the invention are used to diagnose an SSTR-expressing tumor, and subsequently, a complex of β-emitting radionuclide such as $^{188}$Re or $^{186}$Re with the compound is used to treat the tumor.

For diagnostic purposes, an effective diagnostic amount of the diagnostic or radiodiagnostic agent of the invention is administered, preferably intravenously. An effective diagnostic amount is defined as the amount of diagnostic or radiodiagnostic agent necessary to effect localization and detection of the label in vivo using conventional methodologies such as magnetic resonance, computerized tomography, gamma scintigraphy, SPECT, PET, and the like.

For diagnosis using scintigraphic imaging, preferably, $^{99}$Tc-labeled compounds of the invention are administered in a single unit injectable dose. The $^{99}$Tc-labeled compounds provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 50 mCi. The solution to be injected at unit dosage is from about 0.01 mL to about 10 mL. After intravenous administration, imaging in vivo can take place in a matter of a few minutes. However, imaging can take place, if desired, hours or even longer after the radiolabeled compound is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

2. Methods of Treatment

Analogs of the invention provide improved methods of treating any disease or condition that can be treated with a given therapeutic composition, where the "parent" polypeptide is normally cleaved in vivo by a proteinase. Given that proteolysis decreases or eliminates the availability of the therapeutic, and in some instances leads to the production of functionally antagonistic products, the safety and efficacy of many polypeptide therapeutics which can be used to treat particular diseases and conditions is greatly compromised. Accordingly, the methods and compositions of analogs of the invention provide improved methods of treating any of a number of diverse diseases and conditions.

The analogs of the invention possess, in certain embodiments, the ability to lower blood glucose levels, to relieve obesity, to alleviate impaired glucose tolerance, to inhibit hepatic glucose neogenesis, and to lower blood lipid levels (e.g., free fatty acids) and to inhibit aldose reductase. The analogs of the invention, in certain embodiments, are also able to increase islet proliferation and neogenesis, increase glucose-dependent insulin secretion, increase insulin biosynthesis, decrease glucagon secretion, delay gastric emptying, decrease food intake and/or appetite, increase heart function (e.g., left ventricle ejection fraction), increase heart rate, increase systolic blood pressure, decrease vascular resistance (diastolic blood pressure), increase peripheral blood flow, increase sodium excretion in hypernatremic patients (e.g., to decrease Na-dependent hypertension), decrease ischemia/reperfusion injury (e.g., reduce infarct size following a myocardial infarction), decrease neurotoxicity (e.g., neurotoxicity associated with glutamate or kainate excitotoxicity), decrease apoptosis (e.g., in neurons), decrease the prevalence of beta-amyloid proteins and increase spatial and/or associative learning. They are thus useful for, inter alia, the prevention and/or therapy of hyperglycemia, obesity, hyperlipidemia, diabetic complications (including retinopathy, nephropathy, neuropathy, cataracts, coronary artery disease and arteriosclerosis), heart disease, myocardial infarctions, circulatory disorders, neurodegenerative disease (e.g., Alzheimer's disease, Huntington's disease, amyotrophic lateral sclerosis) and furthermore for obesity-related hypertension and osteoporosis. Thus one aspect of the present invention is a method for treating a disease in a patient or subject comprising administering a therapeutically effective amount of one or more GLP-1 analogs disclosed herein.

Analogs of GLP-1 peptides are particularly useful when administered to patient suffering from diabetes mellitus, including Type I and Type II diabetes mellitus, but especially Type II. Diabetes mellitus is a disease characterized by hyperglycemia occurring from a relative or absolute decrease in insulin secretion, decreased insulin sensitivity or insulin resistance. The morbidity and mortality of this disease result from vascular, renal, and neurological complications. An oral glucose tolerance test is a clinical test used to diagnose diabetes. In an oral glucose tolerance test, a patient's physiological response to a glucose load or challenge is evaluated. After ingesting the glucose, the patient's physiological response to the glucose challenge is evaluated. Generally, this is accomplished by determining the patient's blood glucose levels (the concentration of glucose in the patient's plasma, serum or whole blood) for several predetermined points in time.

Thus, in one aspect, the present invention relates to therapeutic and related uses of proteolysis-resistant GLP-1 analogs for treating hyperglycemia, obesity, hyperlipidemia, diabetic complications (including retinopathy, nephropathy, neuropathy, cataracts, coronary artery disease and arteriosclerosis) and furthermore for obesity-related hypertension and osteoporosis.

The invention contemplates the use of analogs in methods of treatment wherein the analog alone constitutes the therapeutic regimen, as well as methods of treatment that utilize administration of one or more analogs as part of a more complex multi-factorial therapeutic regimen. For example, in the case of methods of treating diabetes and/or complications of diabetes, the present invention contemplates methods of treating diabetes by administering a GLP-1 analog. The present invention further contemplates that, in some circumstances, it may be preferably to administer more than one analog. For example, the method of treatment may comprise administration of two or more analogs. Furthermore, the invention contemplates that administration of one or more analogs may be used as part of a complex therapeutic regimen. In the case of a method of treating diabetes or complications of diabetes, an exemplary therapeutic regimen may include administration of one or more analogs, administration of insulin, modulation of diet, and modulation of exercise.

In still a further example of a multi-faceted therapeutic regimen, the invention contemplates the administration of one or more analogs and one or more agents that inhibit the enzymatic activity of the particular enzyme that endogenously cleaves the native protein. In the case of GLP-1, an exemplary method would comprise administration of one or more analogs with one or more inhibitors of DPP IV. Inhibitors of a particular enzyme may be specific (e.g., an inhibitor that modulates only the activity of DPP IV) or the inhibitor may be more promiscuous (e.g., an inhibitor that modulates the activity of multiple serine proteases). Additionally, the invention contemplates the administration of one or more analogs and one or more enzymes that degrade the particular enzyme that endogenously cleaves the native protein. In the case of GLP-1, an exemplary method would comprise administration of one or more peptide analogs with one or more enzymes that degrade DPP IV. Such enzymes may be specific (e.g., an enzyme that only degrades DPP IV) or the enzyme may degrade multiple other protein (e.g., an enzyme that degrades several serine proteases).

(f) Business Methods

Other aspects of the invention provide for certain methods of doing business. In particular, practicing the methods of the invention may identify certain GLP-1 analogs. This technical step, when combined with one of more additional steps, provides for novel approaches to conduct a pharmaceutical, agrochemical, biotechnological, or preferably a life-science business. For example, analogs according to the present invention can be tested for efficacy as therapeutics in a variety of disease models, and the potential therapeutic compositions can then be tested for toxicity and other safety-profiling before formulating, packaging and subsequently marketing the resulting formulation for the treatment of disease. Alternatively, the rights to develop and market such formulations or to conduct such steps may be licensed to a third party for consideration. In certain other aspects of the invention, the analogs thus identified may have utility in the form of information that can be provided to a third party for consideration such that an improved understanding of the function or side effects of said analogs in a biological or therapeutic context is obtained.

In certain embodiments, the initially identified analog can be subjected to further optimization, e.g., to further refine the structure of a lead analog. Such optimization may lead to the development of analogs that combine maximal duration of action with other diserable pharmacological characteristics including: solubility, permeability, bioavailability, toxicity, mutagenicity, and pharmacokinetics.

Structural modifications are typically made to a lead analog to address issues with the parameters listed above. These modifications however, must take into account possible effects on the analog's potency and activity. For example, if the toxicity of a lead analog is high when tested in an animal model, modifications can be made to the analog in an effort to decrease toxicity while maintaining the desired characteristics.

Candidate analogs (whether or not said analogs are modified to alter to improve in vivo characteristics) or combinations thereof, must be tested for efficacy and toxicity in animal models. Such therapeutic profiling is commonly employed in the pharmaceutical arts. Before testing an experimental therapeutic in humans, extensive therapeutic profiling (preclinical testing) must be completed to establish initial parameters for safety and efficacy. Preclinical testing establishes a mechanism of action for the therapeutic, its bioavailability, absorption, distribution, metabolism, and elimination through studies performed in vitro (that is, in test tubes, beakers, petri dishes, etc.) and in animals. Animal studies are used to assess whether the therapeutic will provide the desired results. Varying doses of the experimental therapeutic are administered to test the therapeutic's efficacy, identify harmful side-effects that may occur, and evaluate toxicity.

Briefly, one of skill in the art will recognize that the identification of a candidate analog is a first step in developing a pharmaceutical preparation useful for administration. Administration of an amount of a pharmaceutical preparation comprising said analog effective to treat a condition or disease must be both safe and effective. Early stage drug trials, routinely used in the art, help to address concerns of the safety and efficacy of a potential pharmaceutical. In the specific case of an analog, efficacy of the pharmaceutical preparation could be readily evaluated first in cell culture, and then in a mouse or rat model. Cell culture systems and animal models appropriate for the particular disease indication for which a given analog will be used can be readily selected by one of skill in the art. Briefly, mice or rats could be administered varying doses of said pharmaceutical preparations over various time schedules. The route of administration would be appropriately selected based on the particular characteristics of the agent and on the cell type to which delivery of the analog is desired. Control mice can be administered a placebo (e.g., carrier or excipient alone).

In one embodiment, the step of therapeutic profiling includes toxicity testing of analogs in cell cultures and in animals; analysis of pharmacokinetics and metabolism of the candidate analog; and determination of efficacy in animal models of diseases. In certain instances, the method can include analyzing structure-activity relationship and optimizing lead analogs based on efficacy, safety and pharmacokinetic profiles. The goal of such steps is the selection of analog candidates for pre-clinical studies to lead to filing of Investigational New Drug applications ("IND") with the FDA prior to human clinical trials.

Between lead optimization and therapeutic profiling, one goal is to develop an analog that has a long duration of action relative to native GLP-1 and fragments thereof and can be administered with minimal side-effects. In the case of analogs for in vitro use, exemplary analogs should not be exceptionally toxic to cells in culture, should not be mutagenic to cells in culture, and should not be carcinogenic to cells in culture. In the case of analogs for in vivo use, exemplary analogs should not be exceptionally toxic (e.g., should have only tolerable side-effects when administered to patients), should not be mutagenic, and should not be carcinogenic.

By toxicity profiling is meant the evaluation of potentially harmful side-effects which may occur when an effective amount of a pharmaceutical preparation is administered. A side-effect may or may not be harmful, and the determination of whether a side effect associated with a pharmaceutical preparation is an acceptable side effect is made by the Food and Drug Administration during the regulatory approval process. This determination does not follow hard and fast rules, and that which is considered an acceptable side effect varies due to factors including: (a) the severity of the condition being treated, and (b) the availability of other treatments and the side-effects currently associated with these available treatments. For example, the term cancer encompasses a complex family of disease states related to misregulated cell growth, proliferation, and differentiation. Many forms of cancer are particularly devastating diseases which cause severe pain, loss of function of the effected tissue, and death. Chemotheraputic drugs are an important part of the standard therapy for many forms of cancer. Although chemotherapeutics themselves can have serious side effects including hair loss, severe nausea, weight loss, and sterility, such side effects are considered acceptable given the severity of the disease they aim to treat. In the context of the present invention, whether a side effect is considered significant will depend on the condition to be treated and the availability of other methods to treat that condition.

Toxicity tests can be conducted in tandem with efficacy tests, and mice administered effective doses of the pharmaceutical preparation can be monitored for adverse reactions to the preparation.

One or more analogs, which are proven safe and effective in animal studies, can be formulated into a pharmaceutical preparation. Such pharmaceutical preparations can then be marketed, distributed, and sold. Exemplary analogs and pharmaceutical preparation of such analogs may be marketed and sold alone, or may be sold as a pharmaceutical package and/or kit. Furthermore, in any of the foregoing aspects, a method of conducting a business based on the design of one or more analogs may optionally include a system for billing a patient and/or the patient's insurance provider, as well as a system for collecting appropriate reimbursement from the patient and/or the patient's insurance provider.

EXAMPLES

The following examples are shown by way of illustration and not by way of limitation.

Example 1

Duration of Action of GLP-1 Analogs

DPP-IV cleaves the N-terminal dipeptide from peptides with either Pro or Ala in the penultimate position (P2). Insertion of the unnatural amino acid tent-leucine (Tle), which has a tertiary side chain β-carbon, greatly reduces the rate of cleavage. This is demonstrated in FIG. 1A with three homologous peptides, Ala-Pro-Leu-Ser-Trp-Ser-NH$_2$ (SEQ ID NO: 14), Ala-Pro-Ile-Ser-Trp-Ser-NH$_2$ (SEQ ID NO: 15) and Ala-Pro-Tle-Ser-Trp-Ser-NH$_2$ (SEQ ID NO: 16), which differ only the arrangement of the sidechain atoms of the P3 residue. There was little difference between the rate of cleavage for the Leu and Ile containing peptides (half life 49 and 41 min respectively). No reaction was observed with the Tle containing peptide during a 30 minute digestion.

DPP IV is known to cleave GLP-1 which has an Ala at P2 and Glu at P3. An analog of GLP-1 with Tle replacing the P3 Glu residue is stable to degradation by DPP IV (FIG. 1B). The Glu residue is known to be important for GLP-1 receptor binding and activation. We therefore synthesized another analog with β-dimethyl Asp (DMA) at P3. This modification maintains the acidic group found in the native sequence but introduces a tertiary β-carbon. As shown in FIG. 1B, the Tle- and β-DMA-substituted GLP-1 analogs were resistant to degradation by DPP IV with half-lives greater than 1000 min compared to a half-life of 96 min for native GLP-1.

Figure 2:
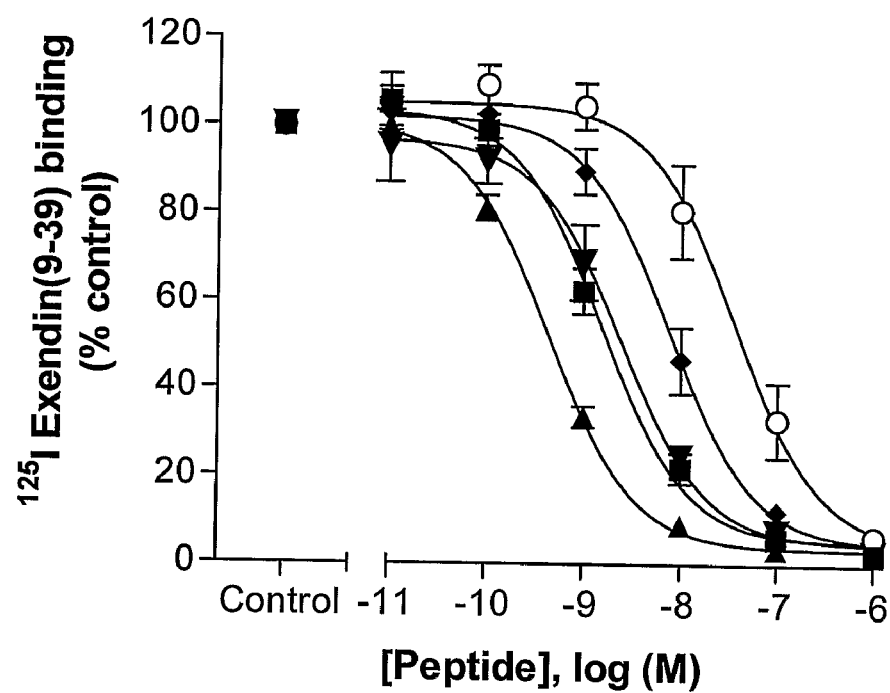
FIG. 2 shows the competition of GLP-1 (■), Exendin-4 (▲), TPA144 (○), TPA1B4 (◆) and P1732 (▼) with $^{125}I$ exendin (9-39) binding in COS-7 cells expressing the human GLP-1 receptor. $IC_{50}$ values were 1.5 nM for GLP-1, 36.3 nM for TPA144, 7.6 nM for TPA1B4, 2.5 nM for P1732 and 0.4 nM for Exendin-40. Data represent the results of independent experiments and are normalized to $^{125}I$ exendin (9-39) binding in the absence of competitor.

Although the modification of the P3 residue of GLP-1 stabilized the peptide, the modifications also reduced the receptor affinity. Nevertheless, attaching amino acid residues from exendin-4 to the carboxy terminus of the peptides improves the affinity of the modified peptides for the GLP-1 receptor and largely compensates for the loss caused by the P3 modifications (FIG. 2). Changing the Glu residue at P3 of GLP-1 to Tle, to produce the peptide referred to as TPA144, resulted in a 20-fold decrease in the affinity for the GLP-1 receptor compared to GLP-1. The IC$_{50}$ increased from 1.5 nM for GLP-1 to 36.3 nM for TPA144. When the P3 residue was β-dimethyl Asp, to form TPA1B4, the decrease in affinity was only about 5-fold. TPA1B4 had an IC$_{50}$ of 7.6 nM. Addition of the carboxy terminal 9 residues of exendin-4 to the end of the TPA1B4 sequence, to form P1732, compensated for the loss of affinity from the P3 DMA residue. The affinity of P1732 is not significantly different than that of GLP-1 (IC$_{50}$ for P1732 was 2.5 nM versus 1.5 nM for GLP-1). Binding of exendin-4 to the GLP-1 receptor was measured for comparison. This peptide binds with small but significant increase in affinity compared to GLP-1, as the IC$_{50}$ value for exendin-4 binding to the GLP-1 receptor was 0.4 nM.

Figure 3:
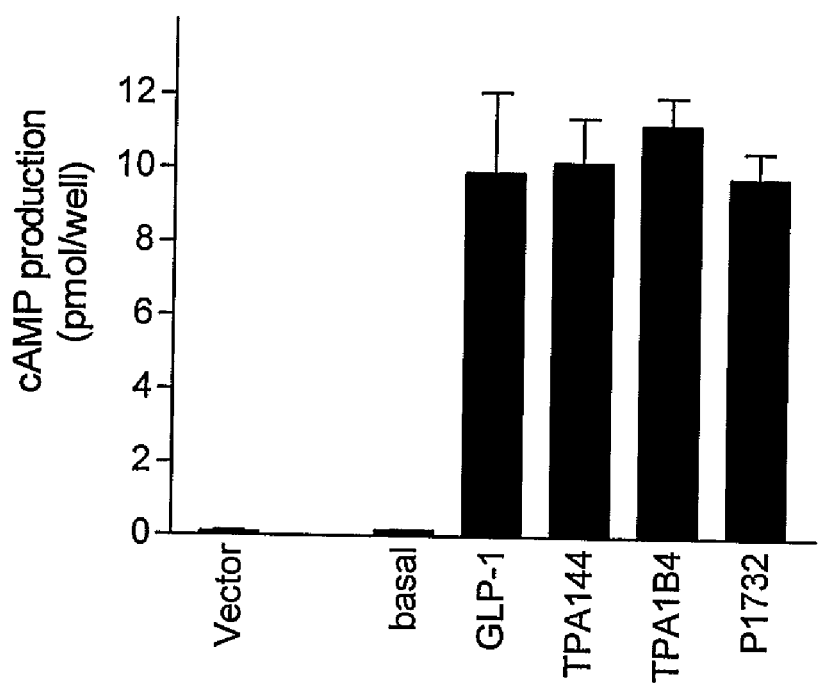
FIG. 3 shows activation of the GLP-1 receptor, as measured by cAMP production. Peptides were tested for agonist activity at a concentration of 300 nM. The data represent the mean±SEM with n=4.
Figure 4:
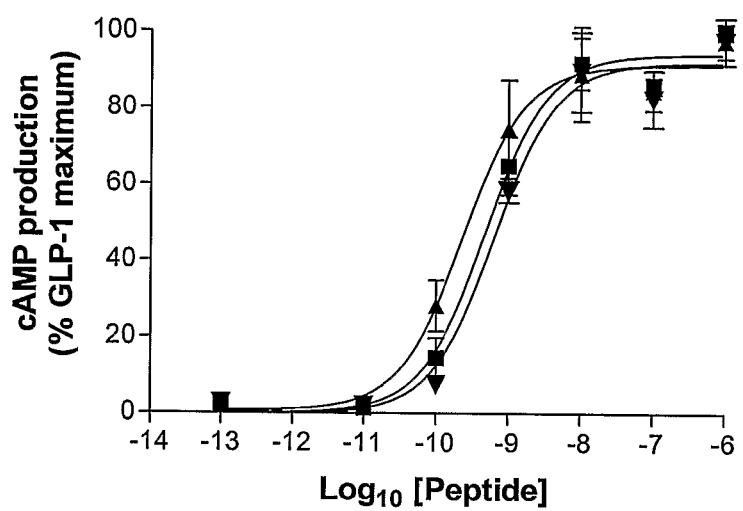
FIG. 4 shows cAMP production in COS-7 cells expressing the human GLP-1 receptor following incubation with various concentrations of GLP-1 (■), P1732 (▼) and Exendin-4 (▲). Data values∓SEM are plotted and fit to a sigmoidal dose-response curve. $EC_{50}$ values obtained from the fitted curves are 0.5 nM, 0.6 nM and 0.2 nM for GLP-1, P1732 and Exendin-4 respectively.

Modifications of GLP-1 do not affect peptide efficacy (FIG. 3). At a high peptide concentration, the amount of GLP-1 receptor activation, as measured by cAMP production, was the same for GLP-1, TPA144, TPA1B4 and P1732. Thus, the P3 GLP-1 analogs with P3 modifications act as full agonists of the GLP-1 receptor. Further extension of the carboxy terminal extension did not diminish this agonist activity. The in vitro potency of P1732 was measured and compared to GLP-1 and exendin-4 by measuring EC$_{50}$ values for receptor activation (FIG. 4). The GLP-1 analog with combined amino- and carboxy-terminal modifications maintains normal potency with an EC$_{50}$ of 0.4-1.1 nM, compared to GLP-1, which had an $EC_{50}$ of 0.3-0.8 nM. Exendin-4 had an $EC_{50}$ that was slightly lower than GLP-1 (0.1-0.5 nM).

Figure 5:
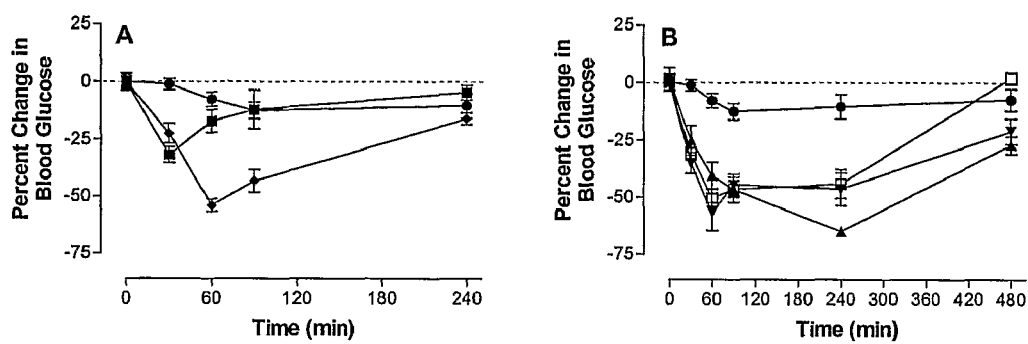
FIG. 5 shows time course of glucose lowering effects, where blood glucose measurements were made before, and at the indicated times after injection of saline (●), or 8 μg of, GLP-1 (■), TPA1B4 (◆), P1732 (▼), DGS65 (□), or Exendin-4 (▲). TPA1B4 with P3 β-dimethyl Asp is compared to GLP-1 (A) and peptide analogs with both P3 and carboxy terminal modifications are compared to exendin-4 (B). At each time point the percent change in blood glucose was determined for 10 mice and the average change±SEM is plotted.

The DPP IV resistant GLP-1 analogs have extended duration of action compared to GLP-1 (FIG. 5A). GLP-1 lowers blood glucose in db mice at 30 minutes post injection but this effect is largely gone by 60 minutes. In contrast, the DPP IV resistant analog TPA1B4 shows a similar effect at 30 minutes but blood glucose continues to decrease for 60 minutes following injection. The blood glucose values at 60 minutes are within the range observed for normal mice. This effect persists for at least 90 minutes. By 4 hours, the blood glucose values return to the hyperglycemic values observed in the control animals.

Exendin-4 has a significantly longer duration of action than GLP-1 or the DPP IV resistant analog TPA1B4. Blood glucose values are reduced in db mice for at least 4 hours following injection (FIG. 5B). By adding the 9 residue C-terminal extension to form P1732, the effect on blood glucose is equivalent to that of exendin-4. To test whether the whole 9 residue extension is required for this effect on the duration of action, the GLP-1 analog DGS65 was prepared with a P3 β-DMA and a 3 residue carboxy terminal extension corresponding to residues 31-33 of exendin-4 (Pro-Ser-Ser). As with exendin-4 and P1732, this peptide lowered blood glucose to normal values in db mice for at least 4 hours with a return to hyperglycemic levels by 8 hours.

Figure 6:
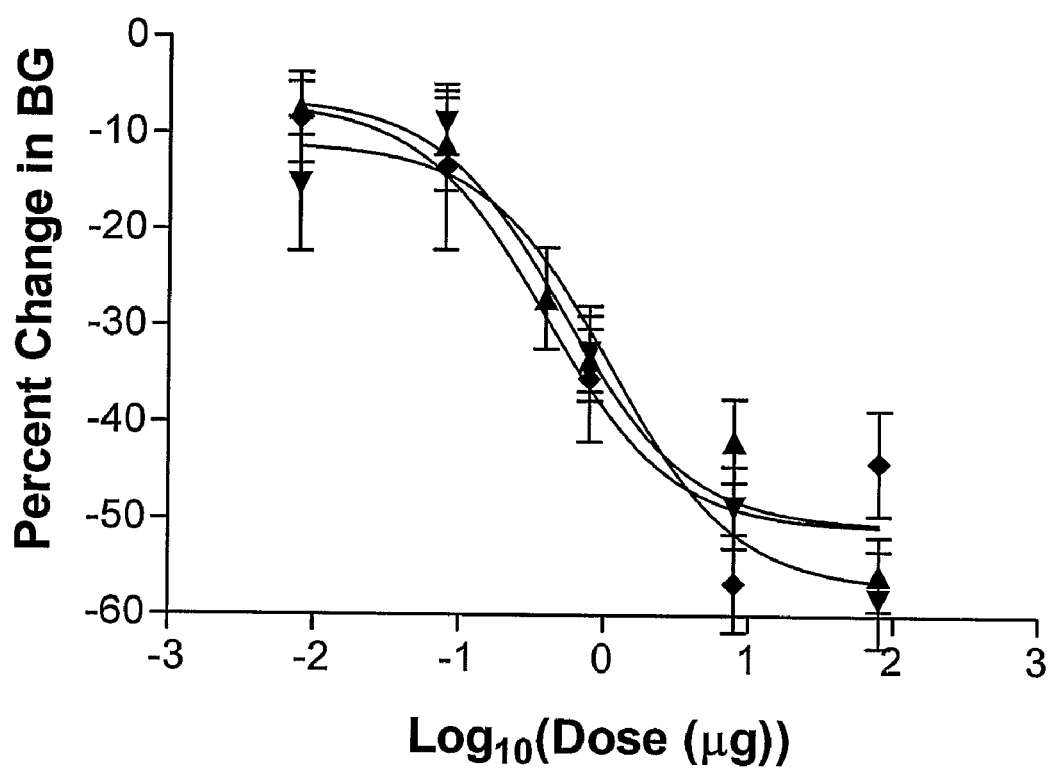
FIG. 6 shows the dose response exhibited by the peptides of Example 1 in diabetic mice. Blood glucose measurements were made before injection of various doses of TPA1B4 (◆), P1732 (▼) and Exendin-4 (▲) and again at 60 minutes post injection. At each dose, the percent change in blood glucose was determined for 10 mice and the average change±SEM is plotted. The data were fit to a sigmoidal dose response curve. $EC_{50}$ values from these fits (and 95% confidence intervals) are 0.4 μg (0.1-1.92 μg) for TPA1B4, 0.5 μg (0.4-3.5 μg) for P1732 and 0.5 μg (0.2-1.2 μg) for exendin-4.

Exendin-4 and the DPP IV resistant GLP-1 analogs P1732 and TPA1B4 were administered to db mice at doses ranging from 0.008 μg to 80 μg to determine the dose dependence of the glucose lowering effect. Blood glucose was measured at 60 minutes after injection, which corresponds to the time of maximal effect at the 8 μg dose. All three peptides showed dose dependence (FIG. 6), with similar $EC_{50}$ values of 0.5 μg for exendin-4, 1.1 μg for P1732 and 0.4 μg for TPA1B4.

The results of Example 1 are summarized in Table 2.

TABLE 2

| Compound | $IC_{50}$ (nM) | $EC_{50}$ (nM) | P3 substitution | C-terminal Extension |
| --- | --- | --- | --- | --- |
| GLP-1 | 1.5 | 0.48 | None | None |
| TPA144 | 36.3 | — | Tle | None |
| TPA1B4 | 7.6 | — | DMA | None |
| P1732 | 2.5 | 0.64 | DMA | PSSGAPPPS (SEQ ID NO: 5) |
| Exendin-4 | 0.4 | 0.23 | — | — |

Example 2

Figure 7:
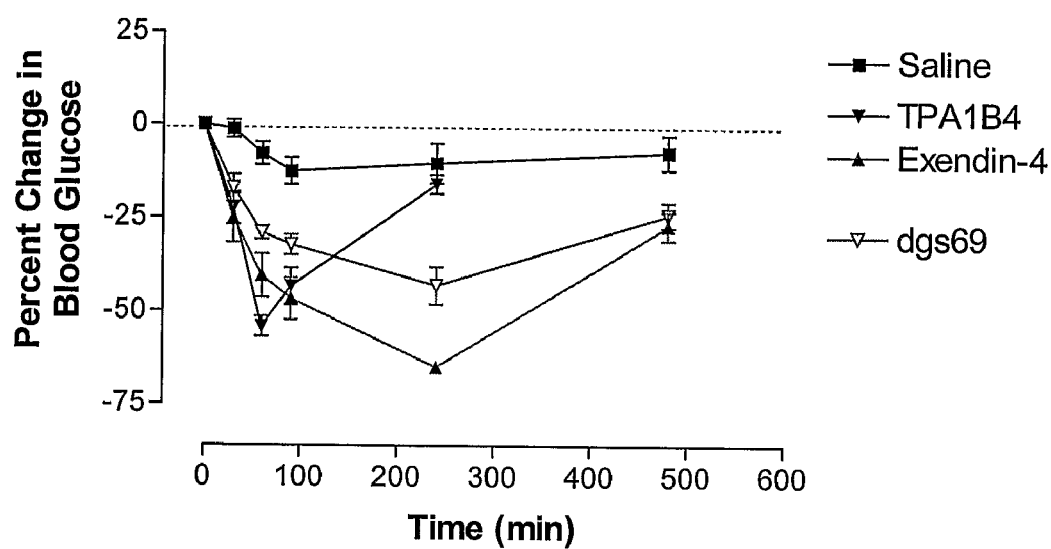
FIG. 7 shows the time course of glucose lowering effects, where blood glucose measurements were made before, and at the indicated times after injection of saline (■), or 8 μg of TPA1B4 (▼), DGS69 (∇), or Exendin-4 (▲). At each time point, the percentage change in blood glucose was determined for 10 mice and the average change±SEM is plotted.

Duration of Action of GLP-1 Analog With Carboxy Terminal Non-Naturally Occurring Amino Acid Residue Peptide DGS69 is homologous to the DPP IV resistant GLP-1 analog TPA1B4. These two peptides both contain β-dimethyl Asp in position 3, which renders them resistant to degradation by DPP IV. DGS69 differs from TPA1B4 in that an unusual amino acid, Biphenyl Alanine (Bip) was added to the carboxy terminus. This single residue addition significantly increased the duration of the blood glucose lowering effect in diabetic mice. The time course of action is compared to that of TPA1B4 and Exendin-4 in FIG. 7. The structures of the peptides are shown below.

```
GLP-1
                                            (SEQ ID NO: 3)
HAEGTFTSDVSSYLEGQAAKEFIAWLVKGR-NH2

Exendin-4
                                            (SEQ ID NO: 8)
HGEGTFTSDLSKQMEEEAVRLFIEWLKNGGPSSGAPPPS-[NH2]

TPA1B4
                                            (SEQ ID NO: 12)
HAXGTFTSDVSSYLEGQAAKEFIAWLVKGR-NH2

DGS69
                                            (SEQ ID NO: 13)
HAXGTFTSDVSSYLEGQAAKEFIAWLVKGRZ-NH2

X = β-dimethyl Asp (DMA)
Z = Biphenyl Alanine (Bip)
```

In summary, it was found that addition of a single unnatural amino acid, Bip, to the carboxy terminus of a DPP IV resistant GLP-1 analog imparts a long duration of action, essentially equal to that of Exendin-4.

All publications, patents and patent applications are herein incorporated by reference in their entirety to the same extent as if each individual publication, patent or patent application was specifically and individually indicated to be incorporated by reference in its entirety.

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims.

We claim:

1. A polypeptide analog comprising:
   a) a base amino acid sequence at least 90% identical to GLP-1-(7-36) (SEQ ID NO: 3); and
   b) one to fifteen amino acid residues attached to the carboxy terminus of the base amino acid sequence, wherein one or more of said amino acid residues is biphenylalanine;

wherein the analog has GLP-1-like activity of longer duration in vivo in humans than native GLP-1-(7-36).

2. The analog of claim 1, wherein the analog retains at least 50 percent of the biological activity of GLP-1-(7-36) (SEQ ID NO: 3).

3. The analog of claim 1, wherein the analog has a base amino acid sequence differing by no more than one residue from the sequence of GLP-1-(7-36) (SEQ ID NO: 3).

4. The analog of claim 3, wherein the analog has a base amino acid sequence identical to GLP-1-(7-36) (SEQ ID NO: 3).

5. A polypeptide analog comprising:
   a) a base amino acid sequence at least 90% identical to GLP-1-(7-36) (SEQ ID NO: 3) in which the amino acid residue in the base amino acid sequence corresponding to the P'$_1$ residue of GLP-1 is an amino acid analog having a tetrasubstituted C$_\beta$ carbon; and
   b) one to fifteen amino acid residues attached to the carboxy terminus of the base amino acid sequence, wherein one or more of said amino acid residues is biphenylalanine;

wherein the analog has GLP-1-like activity of longer duration in vivo in humans than native GLP-1-(7-36).

6. The analog of claim 5, wherein the residue corresponding to the P'$_1$ residue of a DPP IV cleavage site in said analog reduces the susceptibility of the analog to cleavage by DPP IV relative to GLP-1-(7-36).

7. The analog of claim 6, wherein the residue corresponding to the P'$_1$ residue is represented by the following formula:

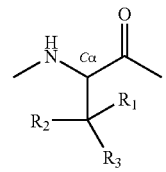

wherein:
   $R_1$ and $R_2$ each independently represent a lower alkyl, heteroalkyl, cycloalkyl, heterocycloalkyl, aryl, alkoxyl, carbonyl, carboxamide, halogen, hydroxyl, amine, or cyano, or $R_1$ and $R_2$ taken together form a ring of 4-7 atoms;
   $R_3$ represents a lower alkyl, a heteroalkyl, amino, alkoxyl, halogen, carboxamide, carbonyl, cyano, thiol, thioalkyl, acylamino, nitro, azido, sulfate, sulfonate, sulfonamido, —(CH$_2$)$_m$—R$_4$, —(CH$_2$)$_m$—OH, —(CH$_2$)$_m$—COOH, —(CH$_2$)$_m$—O-lower alkyl, —(CH$_2$)$_m$—O-lower alkenyl, —(CH$_2$)$_n$—O—(CH$_2$)$_m$—R$_4$, —(CH$_2$)$_m$—S- lower alkyl, —(CH$_2$)$_m$—S-lower alkenyl, —(CH$_2$)$_n$—S—(CH$_2$)$_m$—R$_4$, —(CH$_2$)$_m$—N—C(=NH)NH$_2$, —(CH$_2$)$_m$C(=O)NH$_2$, or —(CH$_2$)$_m$—NH$_2$;

R$_4$ represents, independently for each occurrence, an aryl, aralkyl, cycloalkyl, cycloalkenyl, or non-aromatic heterocyclyl; and m=0, 1 or 2.

8. The analog of claim 7, wherein R$_1$ and R$_2$ each independently represent a lower alkyl or a halogen; and R$_3$ represents a lower alkyl, an aryl, a hydroxyl group, —(CH$_2$)$_m$—COOH, —(CH$_2$)$_m$—NH$_2$, —(CH$_2$)$_m$—N—C(=NH)NH$_2$, —(CH$_2$)$_m$C(=O)NH$_2$, —SH, or —(CH$_2$)$_m$—S—CH$_3$.

9. The analog of claim 8, wherein R$_1$ and R$_2$ each independently represent a methyl, ethyl or propyl.

10. The analog of claim 9, wherein R$_1$ and R$_2$ each represent a methyl.

11. The analog of claim 9, wherein R$_3$ represents a lower alkyl, phenyl, hydroxyphenyl, indole, imidazole, hydroxyl, —COOH, —CH$_2$—COOH, —CH$_2$—CH$_2$—N—C(=NH)NH$_2$, —CH$_2$—C(=O)NH$_2$, —CH$_2$—CH$_2$—C(=O)NH$_2$, —SH, or —CH$_2$—S—CH$_3$.

12. The analog of claim 1 or 5, wherein the analog has a base amino acid sequence at least 95% identical to GLP-1-(7-36) (SEQ ID NO: 3).

13. The analog of claim 12, wherein the analog has the following base amino acid sequence:

```
                                    (SEQ ID NO: 12)
His-Ala-Xaa-Gly-Thr-Phe-Thr-Ser-Asp-Val-Ser-Ser-

Tyr-Leu-Glu-Gly-Gln-Ala-Ala-Lys-Glu-Phe-Ile-Ala-

Trp-Leu-Val-Lys-Gly-Arg,
``` wherein Xaa is beta-dimethylaspartate or tent-leucine.

14. The analog of claim 5, wherein the analog has the following amino acid sequence:

His-Ala-Xaa-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Zaa (SEQ ID NO: 13), wherein Xaa is beta-dimethylaspartate; and Zaa is biphenylalanine.

\* \* \* \* \*

SEQUENCE LISTING

<160> NUMBER OF SEQ ID NOS: 16

<210> SEQ ID NO 1
<211> LENGTH: 28
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys
            20                  25

```
<210> SEQ ID NO 2
<211> LENGTH: 29
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25

<210> SEQ ID NO 3
<211> LENGTH: 30
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 31
<212> TYPE: PRT
<213> ORGANISM: Homo sapiens

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 5
<211> LENGTH: 9
<212> TYPE: PRT
<213> ORGANISM: Heloderma suspectum

<400> SEQUENCE: 5

Pro Ser Ser Gly Ala Pro Pro Pro Ser
1               5

<210> SEQ ID NO 6
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<223> OTHER INFORMATION: See specification as filed for detailed
      description of substitutions and preferred embodiments

<400> SEQUENCE: 6

His Ala Xaa Gly Thr Phe Thr Ser Asp Val Ser Ser Tyr Leu Glu Gly
1               5                   10                  15
```

```
Gln Ala Ala Lys Glu Phe Ile Ala Trp Leu Val Lys Gly Arg Gly
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<223> OTHER INFORMATION: See specification as filed for detailed
      description of substitutions and preferred embodiments

<400> SEQUENCE: 7

His Ala Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 8
<211> LENGTH: 39
<212> TYPE: PRT
<213> ORGANISM: Heloderma suspectum

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 9
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<223> OTHER INFORMATION: See specification as filed for detailed
      description of substitutions and preferred embodiments

<400> SEQUENCE: 9

His Gly Xaa Gly Thr Phe Thr Ser Asp Leu Ser Lys Glu Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 10
<211> LENGTH: 28
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 10

Gly Thr Phe Thr Ser Asp Val Ser Ser Tyr Leu Glu Gly Gln Ala Ala
1               5                   10                  15

Lys Glu Phe Ile Ala Trp Leu Val Lys Gly Arg Gly
            20                  25

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Thr Phe Thr Ser Asp Val Ser Ser Tyr Leu Glu Gly Gln Ala Ala
1               5                   10                  15

Lys Glu Phe Ile Ala Trp Leu Val Lys Gly Arg
            20                  25

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Beta-dimethylaspartate or tert-leucine

<400> SEQUENCE: 12

His Ala Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Beta-dimethylaspartate
<220> FEATURE:
<221> NAME/KEY: MOD_RES
<222> LOCATION: (31)..(31)
<223> OTHER INFORMATION: Biphenyl alanine

<400> SEQUENCE: 13

His Ala Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 14
<211> LENGTH: 6
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 14

Ala Pro Leu Ser Trp Ser
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Pro Ile Ser Trp Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: tert-leucine

<400> SEQUENCE: 16

Ala Pro Leu Ser Trp Ser
1               5
```